(12) United States Patent
Stinson

(10) Patent No.: US 7,540,997 B2
(45) Date of Patent: Jun. 2, 2009

(54) MEDICAL DEVICES HAVING ALLOY COMPOSITIONS

(75) Inventor: Jonathan S. Stinson, Plymouth, MN (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 332 days.

(21) Appl. No.: 11/209,940

(22) Filed: Aug. 23, 2005

(65) Prior Publication Data

US 2007/0044871 A1    Mar. 1, 2007

(51) Int. Cl.
   *C22C 27/06* (2006.01)
(52) U.S. Cl. .................... 420/428; 148/423; 623/1.15
(58) Field of Classification Search ............ 148/237, 148/325, 678; 420/428; 623/1.15
   See application file for complete search history.

(56) References Cited

U.S. PATENT DOCUMENTS

| | | | |
|---|---|---|---|
| 5,401,307 A | 3/1995 | Czech et al. | |
| 5,582,635 A | 12/1996 | Czech et al. | |
| 5,599,385 A | 2/1997 | Czech et al. | |
| 6,238,491 B1 * | 5/2001 | Davidson et al. | 148/237 |
| 2004/0024449 A1 | 2/2004 | Boyle | |
| 2004/0129347 A1 * | 7/2004 | Craig | 148/325 |
| 2005/0145508 A1 | 7/2005 | Larsen et al. | |

FOREIGN PATENT DOCUMENTS

| | | |
|---|---|---|
| WO | WO 00/61203 | 10/2000 |
| WO | WO 01/21229 | 3/2001 |
| WO | WO 02/78764 | 10/2002 |
| WO | WO02/78764 | * 10/2002 |
| WO | WO 2005/039663 | 5/2005 |

OTHER PUBLICATIONS

International Preliminary Report on Patentability mailed Mar. 6, 2008 in PCT/US2006/031658, 7 pages.

* cited by examiner

*Primary Examiner*—Roy King
*Assistant Examiner*—Weiping Zhu
(74) *Attorney, Agent, or Firm*—Fish & Richardson P.C.

(57) ABSTRACT

A medical device includes an alloy having chromium, niobium, and platinum, wherein the alloy forms at least a portion of the medical device.

30 Claims, 2 Drawing Sheets

MEDICAL DEVICES HAVING ALLOY COMPOSITIONS

TECHNICAL FIELD

The invention relates to medical devices including alloy compositions, and the alloy compositions.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced, or even replaced, with a medical endoprosthesis. An endoprosthesis is typically a tubular member that is placed in a lumen in the body. Examples of endoprostheses include stents, stent-grafts, and covered stents.

An endoprosthesis can be delivered inside the body by a catheter that supports the endoprosthesis in a compacted or reduced-size form as the endoprosthesis is transported to a desired site. Upon reaching the site, the endoprosthesis is expanded, for example, so that it can contact the walls of the lumen.

To support a passageway open, endoprostheses are made of materials, such as low-carbon, austenitic stainless steel or Nitinol (a nickel-titanium alloy), having appropriate mechanical properties, such as tensile strength and yield strength.

When the endoprosthesis is advanced through the body, its progress can be monitored, e.g., tracked, so that the endoprosthesis can be delivered properly to a target site. After the endoprosthesis is delivered to the target site, the endoprosthesis can be monitored to determine whether it has been placed properly and/or is functioning properly.

Methods of tracking and monitoring a medical device include X-ray fluoroscopy and magnetic resonance imaging (MRI). MRI is a non-invasive technique that uses a magnetic field and radio waves to image the body. In some MRI procedures, the patient is exposed to a magnetic field, which interacts with certain atoms, e.g., hydrogen atoms, in the patient's body. Incident radio waves are then directed at the patient. The incident radio waves interact with atoms in the patient's body, and produce characteristic return radio waves. The return radio waves are detected by a scanner and processed by a computer to generate an image of the body.

SUMMARY

The invention relates to medical devices including alloy compositions, and the compositions.

In one aspect of the invention, a medical device includes an alloy including chromium, niobium, and platinum, wherein the alloy forms at least a portion of the medical device.

Embodiments may include one or more of the following features. The alloy includes less than about 5 percent by weight of a ferromagnetic element, e.g. iron, nickel, or cobalt. The alloy further includes a first element or a plurality of first elements selected from a group consisting of silicon, calcium, boron, aluminum, nitrogen, carbon, selenium, yttrium, tantalum, and manganese. The alloy can include less than about 2% by weight of individual first elements. The alloy includes from about 5 percent to about 30 percent by weight platinum, e.g. from about 25 percent to about 30 percent by weight platinum. The alloy includes from about 5 percent to about 40 percent by weight niobium, e.g. from about 10 percent to about 20 percent by weight niobium. The alloy includes from about 30 percent to about 90 percent by weight chromium, e.g. from about 40 percent to about 50 percent by weight chromium.

The alloy includes from about 30 percent to about 50 percent by weight chromium; from about 10 percent to about 40 percent by weight niobium; and from about 5 percent to about 30 percent by weight platinum. The alloy includes from about 40 percent to about 50 percent by weight chromium; from about 25 percent to about 30 percent by weight niobium; and from about 25 percent to about 30 percent by weight platinum. The alloy consists essentially of chromium, niobium, and platinum. The alloy includes a binary phase, e.g. a binary phase is selected from the group consisting of $Cr_3Pt$, $Cr_2Nb$, and $Nb_3Pt$.

The device can be in the form of a stent. The device can be selected from the group consisting of a guidewire, a needle, a catheter, an intraluminal filter, a staple, a clip, an orthopedic implant, and dental prosthesis.

In another aspect of the invention, a stent includes an alloy comprising from about 30 percent to about 50 percent by weight chromium, from about 10 percent to about 40 percent by weight niobium, and from about 5 percent to about 30 percent by weight platinum, wherein the alloy forms at least a portion of the stent.

Embodiments may include one or more of the following features. The alloy of the stent includes less than about 5 percent by weight of iron, nickel, or cobalt. The alloy of the stent further includes less than about 2% by weight of a first element selected from a group consisting of silicon, calcium, boron, aluminum, nitrogen, carbon, selenium, yttrium, tantalum, and manganese. The alloy of the stent includes from about 40 percent to about 50 percent by weight chromium, from about 25 percent to about 30 percent by weight niobium, and from about 25 percent to about 30 percent by weight platinum. The alloy of the stent includes a binary phase selected from the group consisting of $Cr_3Pt$, $Cr_2Nb$, and $Nb_3Pt$.

In another aspect, the invention features an alloy including chromium, niobium, and platinum. In some embodiments, the alloy consists essentially of chromium, niobium, and platinum, and has less than about 5 weight percent (e.g., less than about 4 percent, less than about 3 percent, less than about 2 percent, less than about 1 percent, less than about 0.5 percent) of any other element.

Embodiments may include one or more of the following features. The alloy includes less than about 5 percent by weight of a ferromagnetic element, such as iron, nickel, and/or cobalt. The alloy further includes one or more a first element selected from silicon, calcium, boron, aluminum, nitrogen, carbon, selenium, yttrium, tantalum, and manganese. The alloy includes a plurality of first elements. The alloy includes less than about 2% by weight of the first element. The alloy includes from about 5 percent to about 30 percent by weight platinum, for example, from about 25 percent to about 30 percent by weight platinum. The alloy includes from about 5 percent to about 40 percent by weight niobium, for example, from about 25 percent to about 30 percent by weight niobium. The alloy includes from about 30 percent to about 85 percent by weight chromium, for example, from about 40 percent to about 50 percent by weight chromium. The alloy includes from about 30 percent to about 50 percent by weight chromium, from about 10 percent to about 40 percent by weight niobium, and from about 5 percent to about 30 percent by weight platinum. The alloy includes from about 40 percent to about 50 percent by weight chromium, from about 25 percent to about 30 percent by weight niobium, and from about 25 percent to about 30 percent by weight platinum. The alloy consists essentially of chromium, niobium, and platinum. The alloy includes one or more binary phases, such as $Cr_3Pt$, $Cr_2Nb$, and/or $Nb_3Pt$.

Embodiments may include one or more of the following advantages. The alloy compositions have one or more physical and/or mechanical properties, such as radiopacity, MRI compatibility (e.g., low magnetic susceptibility), hardness, strength, stiffness (Young's modulus of elasticity), elongation, and resistance to corrosion, that enhance medical or non-medical applications. For example, the alloy can be formed into a medical device, such as an endoprosthesis. As a result, the endoprosthesis is capable of having a good balance of yield strength and stiffness for a tolerable amount of radial recoil upon expansion to allow good apposition of the stent to the vessel wall, good strength to support a body, and good radiopacity and MRI compatibility, so that the endoprosthesis can be tracked and monitored. The combination of properties allows the alloys to be formed into a variety of products. The alloys can be relatively cost-effective, for example, compared to alloys having high concentrations of precious metal(s).

As used herein, an "alloy" means a substance composed of two or more metals or of a metal and a nonmetal intimately united, for example, by being fused together and dissolving in each other when molten.

Other aspects, features and advantages of the invention will be apparent from the description of the preferred embodiments and from the claims.

DETAILED DESCRIPTION

Figure 1:
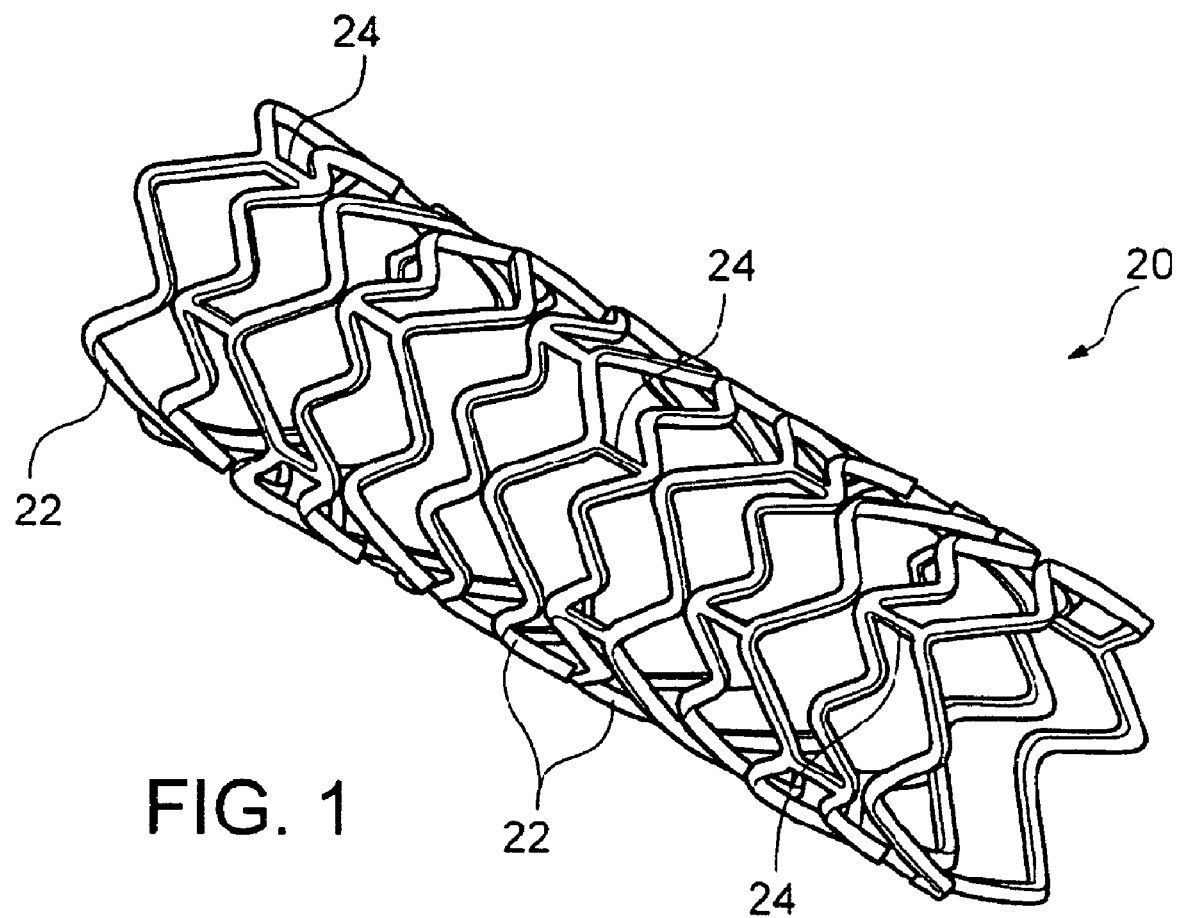
FIG. 1 is a perspective view of an embodiment of a stent.

Referring to FIG. 1, a stent 20 has the form of a tubular member defined by a plurality of bands 22 and a plurality of connectors 24 that extend between and connect adjacent bands. During use, bands 22 are expanded from an initial, small diameter to a larger diameter to contact stent 20 against a wall of a vessel, thereby maintaining the patency of the vessel. Connectors 24 provide stent 20 with flexibility and conformability that allow the stent to adapt to the contours of the vessel.

Stent 20 includes (e.g., is formed of) an alloy whose composition includes chromium, platinum, and niobium. The alloy is capable of providing stent 20 with a balance of yield strength and stiffness for tolerable radial recoil upon crimping onto the balloon catheter and upon expansion in the vessel (for example to have good securement on the balloon catheter while being tracked along the guidewire to the implantation site and to have good apposition against the vessel wall), strength (for example, to support a body lumen), corrosion resistance, radiopacity, and MRI compatibility. For example, chromium has a high stiffness (Young's modulus of elasticity), is a good solid solution strengthener, and aids in corrosion resistance. Platinum also is a good solid solution strengthener, aids in corrosion resistance, as well as provides a high mass absorption coefficient for enhanced radiopacity. Niobium has a low magnetic susceptibility and is compatible with (e.g., soluble in) chromium and platinum. Because niobium also has good radiopacity, inclusion of niobium allows a reduction in the amount of platinum used to achieve a given radiopacity. Furthermore, in some embodiments, the alloy includes less than about 5 percent by weight (e.g., less than about 4 percent, less than about 3 percent, less than about 2 percent, less than about 1 percent, less than about 0.5 percent) of ferromagnetic materials, such as iron, nickel, and/or cobalt. Without wishing to be bound by theory, it is believed that the limited amounts of ferromagnetic materials in the alloy reduce (e.g., minimize or eliminate) interference with MRI techniques, thereby allowing good visualization of stent 20 material (such as blood and tissue) within the lumen of the stent, and material surrounding the stent.

Without wishing to be bound by theory, it is believed that chromium can enhance the corrosion resistance of the alloys, e.g., by increasing the pitting resistance of the alloy. For example, in certain alloys, chromium can form a thin oxide layer on the surface of an alloy that enhances the resistance of the alloy to corrosive attack. The degree of corrosion resistance can be a function of the chromium concentration and the concentrations of other elements in the alloy. The alloy can include from about 30 to about 85 weight percent of chromium. The alloy can include greater than or equal to about 30, about 35, about 40, about 45, about 50, about 55, about 60, about 65, about 70, or about 75 weight percent, and/or less than or equal to about 85, about 80, about 75, about 70, about 65, about 60, about 55, about 50, about 45, about 40, or about 35 weight percent of chromium.

Niobium can enhance the radiopacity of the alloy and provide the alloy with a low magnetic susceptibility. In some embodiments, the alloy includes from about 5 to about 40 weight percent of niobium. For example, the alloys can include greater than or equal to about 10, about 12.5, about 15, about 17.5, about 20, about 22.5, about 25, about 27.5, about 30, about 32.5, about 35 or about 37.5 weight percent, and/or less than or equal to about 40, about 37.5, about 35, about 32.5, about 30, about 27.5, about 25, about 22.5, about 20, about 17.5, about 15, or about 12.5 weight percent of niobium.

Platinum can also enhance the radiopacity of the alloy, as well as provide strength and corrosion resistance. In embodiments, the alloy includes from about 5 to about 30 weight percent of platinum. For example, the alloy can include greater than or equal to about 5, about 7.5, about 10, about 12.5, about 15, about 17.5, about 20, about 22.5, about 25, or about 27.5 weight percent, and/or less than or equal to about 30, about 27.5, about 25, about 22.5, about 20, about 17.5, about 15, about 12.5, about 10, or about 7.5 weight percent of platinum.

In addition to chromium, niobium, and platinum, the alloy can further include one or more (e.g., two, three, four, five, six or more) additional elements capable of assisting with phase stabilization, microcleanliness, and hot workability. Examples of additional element(s) include silicon, calcium, boron, aluminum, nitrogen, carbon, selenium, yttrium, tantalum, and manganese. Each individual additional element can be present up to about 2 percent (e.g., greater than or equal to 0.25 percent, 0.50 percent, 1.0 percent, 1.25 percent, 1.50 percent, or 1.75 percent) by weight in the alloy. In some embodiments, the alloy includes a total of from about 0.10 to about 5.00 weight percent of one or more additional elements.

The alloy can further include one or more microalloyed elements or residual amounts of impurities elements. For example, the alloy may include phosphorus (e.g., 0.025 wt % maximum), sulfur (e.g., 0.010 wt % maximum), vanadium (e.g., about 0.07 wt %), titanium (e.g., 0.002 wt %), and/or copper (e.g., about 0.2 wt %). Other microalloyed and residual elements are possible, which can be a function of the source of the materials.

The alloy can include substantially one homogeneous phase, or include two or more discrete phases. Examples of additional phases include binary phases, such as $Cr_3Pt$, $Cr_2Nb$, and/or $Nb_3Pt$, that can enhance the yield strength of the alloy. The binary phase(s) can be precipitated in the alloy by heat treatment. In some embodiments, the alloy includes from about 1 to about 25 percent of one or more binary phases in the planar area observed in a 1,000× field of view.

The alloy can have a microstructure that is predominantly (greater than 50%) a single-phase solid solution of chromium-platinum-niobium. It is believed that the single-phase microstructure provides the alloy with higher strength and ductility relative to pure chromium.

The alloy can have high corrosion resistance. The relative pitting corrosion resistance can be compared using a pitting resistance equivalent (PRE) as is done with stainless steels, which can be calculated as $$PRE = \% \ Cr + 3.3 \times \% \ Mo$$

ASTM F138 316L grade stainless steel for surgical implants is required to have a PRE≧26.0. This alloy is known to have excellent biocompatibility and corrosion resistance. Cr-10Nb-10Pt does not contain Mo for enhancing pitting corrosion resistance, but contains platinum which is also known to enhance corrosion resistance in chromium (e.g., Alloys cathodically modified with noble metals, Reviews of Applied Electrochemistry 28, J. H. Potgeiter, Journal of Applied Electrochemistry 21 (1991) 471-482). More information about PREs can be found in S. D. Kiser, Preventing Weld Corrosion, *Advanced Materials & Processes*, March 2002, pp. 32-35.

The alloy can also have high hardness and/or high strength. In some embodiments, the alloy has a hardness greater than about 60 Rockwell B e.g., greater than about 65, 70, or 75 Rockwell B. The alloy can have a Young's modulus of elasticity (E) of greater than about 25 msi, e.g., greater than about 28, 30, or 32 msi. The alloy can have an ultimate tensile strength (UTS) of greater than about 60 ksi, e.g., greater than about 70, 80, or 90 ksi. The alloy can have a 0.2% offset yield strength (YS) of greater than about 30 ksi, e.g., 40, 50, or 60 ksi. The alloy can have a percent elongation (% el) of greater than about 10% el, e.g., 15, 20, or 25% el.

Figure 2:
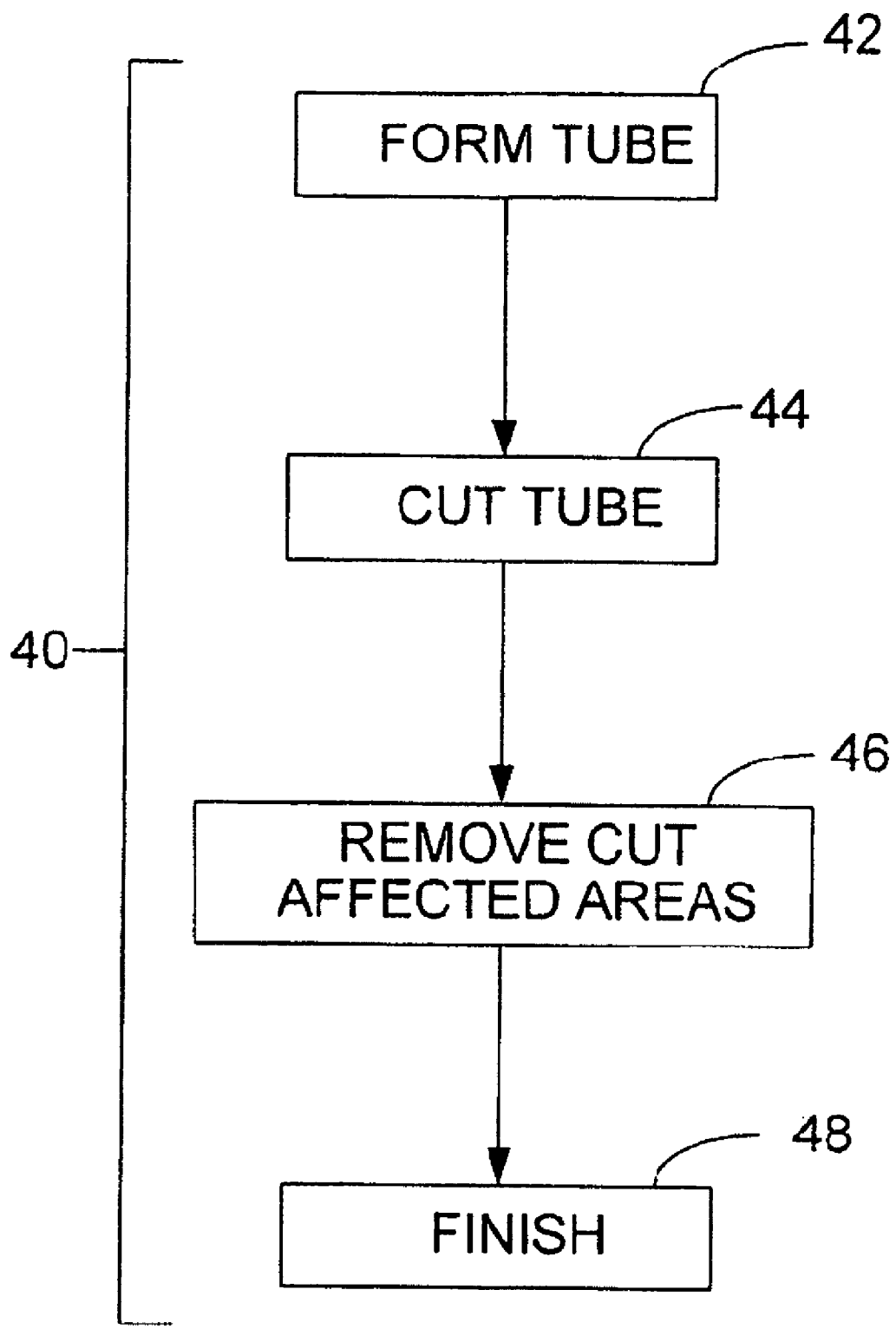
FIG. 2 is a flow chart of an embodiment of a method of making a stent.

Referring to FIG. 2, a method 40 of making stent 20 is shown. Method 40 includes forming a tube (step 42) including the alloy that makes up the tubular member of stent 20. The tube is subsequently cut to form bands 22 and connectors 24 (step 44) to produce an unfinished stent. Areas of the unfinished stent affected by the cutting may be subsequently removed (step 46). The unfinished stent may be finished to form stent 20 (step 48).

The alloy can be synthesized by intimately combining the components of the alloy. For example, a targeted alloy composition can be formed by melting elemental bits or powders in the appropriate concentrations. Melting can be performed at temperatures above about 1800° C. for 10 to 180 minutes using vacuum induction melting (VIM), vacuum arc remelting (VAR), electron beam melting (EBM), plasma melting, vacuum or inert gas plasma deposition. Alloying can be performed in the solid state by blending elemental powders and hot isostatic pressing at temperatures greater than about 1000° C. and less than about 1500° C. for 12 to 36 hours at 5 to 40 ksi pressure, and/or cold pressing and sintering at temperatures greater than about 1000° C. and less than about 1500° C. for 4 to 60 hours. The alloy can be in the form of an ingot, a compact, or a deposit that is subsequently shaped into a feedstock, such as a hollow tubular member. In some embodiments, the alloy is processed (e.g., by heat treatment at 1200° C. for six hours) to homogenize the alloy and/or to yield an alloy with a selected structure and properties.

In some embodiments, the hollow tubular member including the alloy can be drawn through a series of dies with progressively smaller circular openings to plastically deform the member to a targeted size and shape. The plastic deformation strain can harden the member (and increases its yield strength) and elongate the grains along the longitudinal axis of the member. The deformed member can be heat treated (e.g., annealed below or above the recrystallization temperature) to transform the elongated grain structure into a partial or fully recrystallized grain structure, e.g., one including equiaxed grains. Small or fine grains can be formed by heating the member close to the recrystallization temperature for a short time. Large or coarse grains can be formed by heating the member at higher temperatures and/or for longer times to promote grain growth.

Next, bands 22 and connectors 24 of stent 20 are formed, as shown, by cutting the tube (step 44). Selected portions of the tube can be removed to form bands 22 and connectors 24 by laser cutting, as described in U.S. Pat. No. 5,780,807, hereby incorporated by reference in its entirety. In certain embodiments, during laser cutting, a liquid carrier, such as a solvent or an oil, is flowed through the lumen of the tube. The carrier can prevent dross formed on one portion of the tube from re-depositing on another portion, and/or reduce formation of recast material on the tube. Other methods of removing portions of the tube can be used, such as mechanical machining (e.g., micro-machining), electrical discharge machining (EDM), and photoetching (e.g., acid photoetching).

In some embodiments, after bands 22 and connectors 24 are formed, areas of the tube affected by the cutting operation above can be removed (step 46). For example, laser machining of bands 22 and connectors 24 can leave a surface layer of melted and resolidified material and/or oxidized metal that can adversely affect the mechanical properties and performance of stent 20. The affected areas can be removed mechanically (such as by grit blasting or honing) and/or chemically (such as by etching or electropolishing). In some embodiments, the tubular member can be near net shape configuration after step 46 is performed. "Near-net size" means that the tube has a relatively thin envelope of material that is removed to provide a finished stent. In some embodiments, the tube is formed less than about 25% oversized, e.g., less than about 15%, 10%, or 5% oversized.

The unfinished stent is then finished to form stent 20 (step 48). The unfinished stent can be finished, for example, by electropolishing to a smooth finish. Since the unfinished stent can be formed to near-net size, relatively little of the unfinished stent need to be removed to finish the stent. As a result, further processing (which can damage the stent) and costly materials can be reduced. In some embodiments, about 0.0001 inch of the stent material can be removed by chemical milling and/or electropolishing to yield a stent.

Stent 20 can be of a desired shape and size (e.g., coronary stents, aortic stents, peripheral vascular stents, gastrointestinal stents, urology stents, and neurology stents). Depending on the application, stent 20 can have a diameter of between, for example, 1 mm to 46 mm. In certain embodiments, a coronary stent can have an expanded diameter of from about 2 mm to about 6 mm. In some embodiments, a peripheral stent can have an expanded diameter of from about 5 mm to about 24 mm. In certain embodiments, a gastrointestinal and/or urology stent can have an expanded diameter of from about 6 mm to about 30 mm. In some embodiments, a neurology stent can have an expanded diameter of from about 1 mm to about 12 mm. An abdominal aortic aneurysm (AAA) stent and a thoracic aortic aneurysm (TAA) stent can have a diameter from about 20 mm to about 46 mm. Stent 20 can be balloon-expandable, or a combination of self-expandable and balloon-expandable (e.g., as described in U.S. Pat. No. 5,366, 504).

In use, stent 20 can be used, e.g., delivered and expanded, using a catheter delivery system. Catheter systems are described in, for example, Wang U.S. Pat. No. 5,195,969, Hamlin U.S. Pat. No. 5,270,086, and Raeder-Devens, U.S. Pat. No. 6,726,712. Stents and stent delivery are also exemplified by the Radius® or Symbiot® systems, available from Boston Scientific Scimed, Maple Grove, Minn.

While a number of embodiments have been described above, the invention is not so limited.

As an example, while stent 20 is shown as being formed wholly of the alloy, in other embodiments, the alloy forms one or more selected portions of the medical device. For example, stent 20 can include multiple layers in which one or more layers include the alloy, and one or more layers do not include the alloy, e.g., 316L stainless steel. Stents including multiple layers are described, for example, in published patent application 2004-0044397, and Heath, U.S. Pat. No. 6,287,331.

Stent 20 can be a part of a covered stent or a stent-graft. For example, stent 20 can include and/or be attached to a biocompatible, non-porous or semi-porous polymer matrix made of polytetrafluoroethylene (PTFE), expanded PTFE, polyethylene, urethane, or polypropylene.

Stent 20 can include a releasable therapeutic agent, drug, or a pharmaceutically active compound, such as described in U.S. Pat. No. 5,674,242, U.S. Ser. No. 09/895,415, filed Jul. 2, 2001, and U.S. Ser. No. 10/232,265, filed Aug. 30, 2002. The therapeutic agents, drugs, or pharmaceutically active compounds can include, for example, anti-thrombogenic agents, antioxidants, anti-inflammatory agents, anesthetic agents, anti-coagulants, and antibiotics.

In some embodiments, a stent can be formed by fabricating a wire including the alloy, and knitting and/or weaving the wire into a tubular member.

The alloys can be used to form other medical devices, such as those that benefit from having high strength to resist overloading and fracture, high corrosion resistance, and/or biocompatibility (e.g., capable of being implanted in a body for long periods (such as greater than ten years)), particularly medical implants and devices that will be used with fluoroscopy and/or MRI during a medical procedure or when patients will be subjected to follow-up MRI imagery. For example, the alloys can be used to manufacture other endoprostheses. The alloys can be used in filters such as removable thrombus filters described in Kim et al., U.S. Pat. No. 6,146,404, which is hereby incorporated by reference; in intravascular filters such as those described in Daniel et al., U.S. Pat. No. 6,171,327, which is hereby incorporated by reference; and vena cava filters such as those described in Soon et al., U.S. Pat. No. 6,342,062, which is hereby incorporated by reference.

The alloys can be used to form a guidewire (such as a Meier Steerable Guide Wire (for AAA stent procedure)), an ASAP Automated Biopsy System (e.g., for a stylet and/or a cannula, as described in U.S. Pat. Nos. 4,958,625, 5,368,045, and 5,090,419), or a hypotube of a catheter (e.g., a balloon catheter).

The alloys can also be used to manufacture cutting elements, such as those carried by a medical balloon catheter described in U.S. Ser. No. 10/335,604, filed Jan. 2, 2003, and U.S. Pat. Nos. 5,209,799, and 5,336,234. The hardness and strength of the alloys can reduce edge rounding (which can decrease sharpness) and deformation of the product shape. Also, in some cases, the relatively high corrosion resistance of the alloys allows the instruments to be exposed to repeated steam autoclave sterilization cycles. As a result, the instruments can be reused more, and the cost of replacement is reduced.

Still other examples of medical devices include, needles, catheters, staples, wires used for wound closure, clips, orthopedic devices (such as hip stems and knee trays), and dental prostheses.

The following examples are illustrative and not intended to be limiting.

EXAMPLE 1

Cr-10Nb-10Pt Strip Material and Stent Manufacture

An arc melter was used to make a Cr-10Nb-10Pt alloy ingot.

The Cr-10Nb-10Pt ingot was made by melting high purity virgin elemental charge materials. The charge materials were procurred from Goodfellow Cambridge Limited.

TABLE 1

| Material | Goodfellow P/N | Purity | Form | Dimension | Temper |
|---|---|---|---|---|---|
| Chromium | CR006115 | 99.95% | Pellets | 10 mm | N/A |
| Niobium | NB007910 | 99.9% | Rod | 2 mm dia. | annealed |
| Platinum | PT005156 | 99.99% | Wire | 1 mm dia. | annealed |

Table 1 shows the charge materials used in Cr-10Nb-10Pt alloy melting. The pure charge materials were cut and weighed according to an aim alloy formulation of 80 weight percent chromium, 10 weight percent niobium, and 10 weight percent platinum for a total ingot weight of 70 grams. After cleaning with alcohol, the charge materials were loaded into the water-cooled copper hearth plate ingot cavity of the arc melting furnace: a Materials Research Furnaces (MRF) model ABJ-900 inert-gas arc melter. The arc melter consisted of a water cooled copper hearth plate with multiple cavities for charge material placement. Once loaded, the charge materials and copper hearth were sealed inside a bell chamber for melting. After the chamber was evacuated with a vacuum pump and argon back-filled multiple times, the arc melter's power supply was started and a tungsten electrode was used to strike an arc with the charge materials and copper hearth. Melting was performed while using a maximum power supply current output of 400 A. During melting, a constant flow (10 to 30 L/min) of high purity argon gas was passed through the chamber to protect the charge metal from atmospheric contaminants (e.g., O and N). The charge materials were heated and melted until they appeared to have completely mixed to form one solid ingot. Once melting was complete, the newly formed ingot was allowed to cool under protection of the argon cover gas before removing it from the furnace chamber. The ingot was remelted twice in an attempt to homogeneously mix the charge materials.

After melting, the Cr-10Nb-10Pt ingot measured approximately 3.5" long×0.6" wide×0.3" thick. The ingot was vacuum annealed at 1200° C. for 1 hour. The heat treatment was performed to bring into solution any second phases that may have formed during ingot solidification and cooling in the arc melter. The ingot was then machined to a thickness of 0.2" for hot rolling.

Binary phase diagrams were reviewed for Cr—Nb, Cr—Pt, and Nb—Pt. Table 2 shows the liquidus temperatures obtained from the phase diagrams.

TABLE 2

| Element or Alloy: | Liquidus Temperature, ° C. |
|---|---|
| Cr | 1875 |
| Nb | 2468 |
| Pt | 1769 |
| Cr—10Pt | 1700 |
| Cr—10Nb | 1800 |
| 50Pt—50Nb | 1950 |

The dendritic ingot microstructure was expected to consist of Cr—Nb—Pt dendrite arms and Nb—Pt enriched interdendritic regions. This hypothesis is based upon the liquidus temperatures which indicate that if elemental segregation occurs, chromium-niobium-platinum alloy should solidify first and Nb—Pt alloy would solidify last upon cooling from the liquid phase.

According to the Nb—Pt phase diagram, the solid phase interdendritic region could be $Nb_3Pt$ or $Nb_2Pt$ intermetallics. This material would likely be brittle. If the ingot were strained, fracture would likely occur through the intermetallics with little plastic deformation.

Microstructural analysis of the as-cast ingot revealed a dendritic microstructure with the dendritic arms being darker than the interdendritic regions when imaged with backscattered electrons in the Scanning Electron Microscope (SEM). Brighter areas are typically associated with heavy elements when imaged in this manner. SEM Energy Dispersive X-ray Spectroscopy (EDS) spectra taken of the dendrite arms and interdendritic regions revealed that the dendrites were chromium-rich Cr—Nb—Pt and the interdendritic regions were Nb—Pt rich Cr—Nb—Pt.

The ASTM E384 Vickers microhardness of the ingot microstructural specimen was measured and converted to 77 Rockwell B. This converts to a roughly estimated ultimate tensile strength of about 68 ksi using conversion tables for steels since one is not available for chromium alloys.

In order to be able to hot or cold work the ingot to produce strip for materials characterization testing or stent tubing fabrication, the ingot was homogenization heat treated to reduce the elemental concentration gradients between the dendrites and interdendritic regions and thereby eliminate the brittle intermetallic phase(s). Homogenization of the ingot was performed in a partial pressure of argon gas at 1200° C. for 18 hours. The partial pressure of argon gas is intended to minimize the chromium vaporization that would occur at 1200° C. in high vacuum. The process is to perform metallography on the homogenized material after 6, 12, and 18 hours to see when the interdendritic regions appears less segregated via SEM backscattered electron compositional imaging.

When the concentration gradient qualitatively looks significantly reduced, hot rolling is initiated. Hot rolling of the ingot can be performed by heating to red hot in air or with the ingot encapsulated by 0.006" thick 316 stainless steel strip and passed through rollers set a incrementally smaller gaps until a thickness of 0.025" is obtained. Between 15% total reductions, the ingot is annealed or stress relief heat treated to eliminate or reduce strain hardening produced during rolling and to return the material to a plastically deformable condition.

After rolling, the 0.0052" thick strip can be machined to produce flat "dog-bone" shaped specimens for tensile testing. Stent strut patterns can be laser machined into the strip. Post-laser dross removal and electropolishing can be performed to bring the strut pattern to finished dimensions. The strip can then be rolled into the tubular stent shape and crimped onto a balloon catheter.

EXAMPLE 2

Cr-10Nb-10Pt Seamless Tubing and Stent Manufacture

A total of 20 pounds of niobium, platinum, and chromium can be weighed out for the alloy formulation of 80 weight percent chromium, 10 weight percent niobium, and 10 weight percent platinum. The charge materials can be loaded into the hearth of a vacuum electron beam melter and melted to form the liquid alloy. Upon solidification and cooling below 200° C., the ingot would be removed from the EB melter and subjected to two vacuum arc remelting operations to refine the cast microstructure and improve microcleanliness. The triple melted ingot can be coated with glass lubricant and charged into an extrusion press and heated to 1250° C. The hydraulic extrusion press can be used to convert the 3 inch diameter ingot to a 2.5 inch diameter billet. A second extrusion operation can be performed convert the 2.5 inch diameter billet to a 2 inch diameter billet. The billet can then be homogenized at 1200° C. for 18 hours in a partial pressure of argon gas. The homogenized billet can then be gun drilled to produce a 1.0" diameter inner diameter along the longitudinal centerline. The billet outer diameter can be machined to 1.8" diameter such that it is highly concentric with the gun drilled inner diameter.

The hollow rod can be pilgered at room temperature to reduce the OD to 1.25" diameter with 1200° C./1-hour 10% reduction in diameter interpass anneals in a partial pressure of argon gas. The 1.25" diameter pilgered tubing can then be mandrel drawn in straight lengths with 1200° C./30-minute 10% reduction in diameter interpass anneals in a partial pressure of argon gas. At 0.6643" OD, the mandrel drawn tubing can be floating plug drawn in straight lengths with 1200° C./30-minute 10% reduction in diameter interpass anneals in a partial pressure of argon gas until an OD of 0.083" and a wall thickness of 0.0052" are reached.

Stent strut patterns can be laser machined into the seamless drawn tubing. Post-laser dross removal and electropolishing can be performed to produce finished stent dimensions. The stents can be crimped onto balloon catheters.

All publications, references, applications, and patents referred to herein are incorporated by reference in their entirety.

Other embodiments are within the claims.

What is claimed is:

1. A medical device comprising an alloy comprising from about 30 percent to about 90 percent by weight chromium, from about 5 percent to about 40 percent by weight niobium, and platinum, wherein the alloy forms at least a portion of the medical device.

2. The device of claim 1, wherein the alloy comprises less than about 5 percent by weight of a ferromagnetic element.

3. The device of claim 1, wherein the alloy comprises less than about 5 percent by weight of iron, nickel, or cobalt.

4. The device of claim 1, wherein the alloy further comprises a first element selected from a group consisting of silicon, calcium, boron, aluminum, nitrogen, carbon, selenium, yttrium, tantalum, and manganese.

5. The device of claim 4, wherein the alloy comprises a plurality of first elements.

6. The device of claim 4, wherein the alloy comprises less than about 2% by weight of the first element.

7. The device of claim 1, wherein the alloy comprises from about 5 percent to about 30 percent by weight platinum.

8. The device of claim 1, wherein the alloy comprises at least about 5 percent by weight platinum.

9. The medical device of claim 8, wherein the alloy comprises:
from about 30 percent to about 50 percent by weight chromium; and
from about 5 percent to about 40 percent by weight niobium.

10. The device of claim 1, wherein the alloy comprises from about 25 percent to about 30 percent by weight platinum.

11. The device of claim 1, wherein the alloy comprises at least about 25 percent by weight platinum.

12. The device of claim 1, wherein the alloy comprises from about 10 percent to about 20 percent by weight niobium.

13. The device of claim 1, wherein the alloy comprises from about 40 percent to about 50 percent by weight chromium.

14. The medical device of claim 1, wherein the alloy comprises:
from about 30 percent to about 50 percent by weight chromium;
from about 10 percent to about 40 percent by weight niobium; and
from about 5 percent to about 30 percent by weight platinum.

15. The medical device of claim 1, wherein the alloy comprises:
from about 40 percent to about 50 percent by weight chromium;
from about 25 percent to about 30 percent by weight niobium; and
from about 25 percent to about 30 percent by weight platinum.

16. The device of claim 1, wherein the alloy consists essentially of chromium, niobium, and platinum.

17. The device of claim 1, wherein the alloy comprises a binary phase.

18. The device of claim 17, wherein the binary phase is selected from the group consisting of $Cr_3Pt$, $Cr_2Nb$, and $Nb_3Pt$.

19. The device of claim 1, in the form of a stent.

20. The device of claim 1, wherein the device is selected from the group consisting of a guidewire, a needle, a catheter, an intraluminal filter, a staple, a clip, an orthopedic implant, and dental prosthesis.

21. A stent, comprising
an alloy comprising from about 30 percent to about 50 percent by weight chromium, from about 10 percent to about 40 percent by weight niobium, and platinum, wherein the alloy forms at least a portion of the stent.

22. The stent of claim 21, wherein the alloy comprises less than about 5 percent by weight of iron, nickel, or cobalt.

23. The stent of claim 21, wherein the alloy further comprises less than about 2% by weight of a first element selected from a group consisting of silicon, calcium, boron, aluminum, nitrogen, carbon, selenium, yttrium, tantalum, and manganese.

24. The stent of claim 21, wherein the alloy comprises from about 40 percent to about 50 percent by weight chromium, from about 25 percent to about 30 percent by weight niobium, and from about 25 percent to about 30 percent by weight platinum.

25. The stent of claim 21, wherein the alloy comprises a binary phase selected from the group consisting of $Cr_3Pt$, $Cr_2Nb$, and $Nb_3Pt$.

26. The stent of claim 21, wherein the alloy comprises from about 5 percent to about 30 percent by weight platinum.

27. The stent of claim 21, wherein the alloy comprises at least about 5 percent by weight platinum.

28. The stent of claim 21, wherein the alloy comprises at least about 25 percent by weight platinum.

29. A medical device comprising an alloy comprising chromium, niobium, and platinum, the alloy comprising a binary phase, wherein the binary phase is selected from the group consisting of $Cr_3Pt$, $Cr_2Nb$, and $Nb_3Pt$, wherein the alloy forms at least a portion of the medical device.

30. A medical device comprising an alloy consisting essentially of chromium, niobium, and platinum, wherein the alloy forms at least a portion of the medical device.

* * * * *

UNITED STATES PATENT AND TRADEMARK OFFICE
CERTIFICATE OF CORRECTION

PATENT NO. : 7,540,997 B2
APPLICATION NO. : 11/209940
DATED : June 2, 2009
INVENTOR(S) : Jonathan S. Stinson It is certified that error appears in the above-identified patent and that said Letters Patent is hereby corrected as shown below:

On the Title Page

Item [*] Notice: Subject to any disclaimer, the term of this patent is extended or adjusted under 35 USC 154(b) by (332) days Delete the phrase "by 332 days" and insert -- by 505 days --

Signed and Sealed this

Thirteenth Day of July, 2010

David J. Kappos
*Director of the United States Patent and Trademark Office*